(12) United States Patent
Bachman et al.

(10) Patent No.: US 7,704,515 B2
(45) Date of Patent: Apr. 27, 2010

(54) COMPOSITION AND METHOD TO IMPROVE QUALITY AND YIELD OF MEAT PRODUCTS

(75) Inventors: Stephen E. Bachman, Amarillo, TX (US); Michael E. Hubbert, Sparks, NV (US)

(73) Assignee: Ganado Research, L.L.C., Amarillo, TX (US)

( * ) Notice: Subject to any disclaimer, the term of this patent is extended or adjusted under 35 U.S.C. 154(b) by 1317 days.

(21) Appl. No.: 10/510,202

(22) PCT Filed: Apr. 2, 2003

(86) PCT No.: PCT/US03/10002

§ 371 (c)(1),
(2), (4) Date: May 19, 2005

(87) PCT Pub. No.: WO03/084345

PCT Pub. Date: Oct. 16, 2003

(65) Prior Publication Data

US 2005/0232975 A1 Oct. 20, 2005

(51) Int. Cl.
*A61K 9/00* (2006.01)
(52) U.S. Cl. .......................... 424/400; 424/401; 426/2; 426/805
(58) Field of Classification Search .............. 424/400, 424/401, 581, 93.51, 750; 426/2
See application file for complete search history.

(56) References Cited

U.S. PATENT DOCUMENTS

| 4,647,672 A | * | 3/1987 | Seib et al. ................... 549/222 |
| 5,110,950 A | | 5/1992 | Seib et al. |
| 5,118,817 A | | 6/1992 | Yoshida et al. |
| 6,022,566 A | * | 2/2000 | Miller ............................ 426/2 |
| 6,103,267 A | | 8/2000 | Mitchnick et al. |
| 6,352,713 B1 | * | 3/2002 | Kirschner et al. ............ 424/441 |
| 2002/0136778 A1 | * | 9/2002 | Claycamp et al. ........... 424/581 |

OTHER PUBLICATIONS

Peacock et al, Comparative Feeding Value of Dried Citrus Pulp, Corn Feed Meal and Ground Snapped Corn for Fattening Steers in Drylot, Dec. 1959, University of Florida, IFAS Extenstion, BUL616.*
O'Keefe, Ascorbic acid and stable ascorbate esters as sources of vitamin C in aquaculture feeds, ASA Techinical Bulletin vol. AQ48-2001.*
Stanton, "Feed Composition for Cattle and Sheep", Colorado University State—Livestock Series, Oct. 1999, pp. 1-5;.
O'Keefe, "Ascorbic Acid and Stable Ascorbate Esters as Sources of Vitamin C in Aquaculture Feeds", ASA Technical Bulletin, vol. AQ48-2001, pp. 1-9;.

* cited by examiner

*Primary Examiner*—Michael G Hartley
*Assistant Examiner*—Micah-Paul Young
(74) *Attorney, Agent, or Firm*—Dale F. Regelman; Quarles & Brady LLP (57) ABSTRACT

A method to increase the hot carcass weight of a meat-producing animal. The method orally administers Vitamin C to a meat-producing animal between about 2 and about 48 hours prior to harvest. The animal is then harvested and a hot carcass is prepared from that harvested animal.

16 Claims, 8 Drawing Sheets

COMPOSITION AND METHOD TO IMPROVE QUALITY AND YIELD OF MEAT PRODUCTS

FIELD OF THE INVENTION

Applicants' invention relates to a composition and method to increase the quality of meat by reducing cellular weep post harvest and to increase the dressing percent of meat-producing animals, i.e. to increase the yield of meat products from meat-producing animals.

BACKGROUND OF THE INVENTION

Stress can be associated with gathering, movement, weather, noise, or any activity that tends to increase fear and/or anxiety. Regarding meat production livestock, the harvest of those animals comprises a major incidence of anxiety and stress. Such pre-harvest stress results in decreased meat quality, sometimes referred to as "dark cutting" meat. One embodiment of Applicants' method reduces the incidence of "dark cutting" meat, reduces cellular weep post harvest, and increases the dressing percent of cattle.

A phenomenon often called "dark cutting" costs the Beef industry about $5.81 per head marketed, or about $162,000,000 in the year 2000. It impacts the 3% of the cattle marketed. One embodiment of the present invention comprises a composition administered pre-harvest to animals to reduce the occurrence of dark-cutting meat. Such meat-producing animals include, for example, ruminants such as bovine, ovine, and caprine animals. The invention further relates to methods to administer Applicants' composition, where those methods include adding Applicants' composition to the animal's feed, direct oral administration, and/or nasal administration.

The phenomenon of transformation of muscle into meat after slaughtering animals rests on glycogenolysis, which results in the accumulation of lactic acid in the muscle fiber. The pH of the muscle decreases to reach values normally less than 6. It is known, however, that for certain muscles an anomaly exists in the acidification process after death, which is manifested by a failure of the pH of the meat product to eventually decrease to less than 6. These continuously high-pH meats are recognizable by their deep red color, sometimes almost black, which justifies their being named as dark-cutting meat, or DFD meats (Dry, Firm, Dark).

This phenomenon of high-pH is explained particularly by a premature exhaustion of the stock of muscle glycogen before slaughter, which results in an insufficient lactic acid level, and hence, an insufficient lowering of the pH: the latter is then greater than or equal to 6. The post-mortem biochemical reactions which arise there from are responsible for the mediocre quality of this meat.

In fact, apart from the color, the high-pH has other unfavorable consequences on the meat, such as considerable water retention capacity, mediocre organoleptic properties and especially poor preservation. It is well established that dark-cutting meats are considered defective, and are subject to notable commercial depreciation. They represent, therefore, an economic problem prejudicial to the meat industry.

The exhaustion of the stock of glycogen, recognized as being at the origin of the occurrence of these dark-cutting meats, is principally due to stress and to the physical efforts of the animal before slaughter. Various studies have enabled preventive measures to be discovered against the occurrence of dark-cutting meats, which measures seek to control the extrinsic factors causing stress in the animal, and consequently, excessive consumption of muscular glycogen.

These measures consist particularly in not mixing animals of diverse origin, of optimizing the conditions of unloading, reducing the transport time as well as the stalling at the abattoir. However such measures, even if they contribute to limiting the causes of the appearance of dark-cutting meat, have not eliminated this phenomenon.

The American system will penalize black cutter (black color) beef by no more than one full grade (i.e. Prime to Choice, Choice to Select, or Select to Standard). Dark cutter (dark color) beef will be discounted by less than one full grade (i.e. High Choice to Low Choice). It is therefore possible for dark colored beef to be graded Choice, Select, or Standard in the United States. The Canadian grading system will automatically remove all dark cutter beef from the four high quality grades (A/AA/AAA/Prime) to the B4 grade.

What is needed is a composition, and method using that composition, that increases the weight of saleable meat products from meat-producing animals, minimizes the cellular weep of those meat products harvest, and increases the water content of those meat products.

SUMMARY OF THE INVENTION

Applicants' invention includes a composition which includes Vitamin C. In certain embodiments, Applicants' composition further includes cane molasses and dried citrus pulp. Applicants' invention further includes a method to increase the hot carcass weight of an animal. Applicants' method administers Vitamin C to a meat-producing animal between about 2 and about 48 hours prior to harvest. The animal is then harvested and a hot carcass is prepared from that harvested animal.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Applicants' invention includes a composition and method to increase the hot carcass weight of a meat-producing animal, i.e. increase the weight of saleable meat products obtained from that meat-producing animal; increase for up to about 3 hours the pH of meat products obtained from that hot carcass; increase the water content of meat products obtained from that hot carcass; and decrease the drip loss of meat products obtained from that hot carcass.

In certain embodiments, Applicants' composition includes L-ascorbic acid, i.e. Vitamin C or compound I.

I

Crystalline L-ascorbic acid is reasonably stable when dry and in pure form. However, it can be readily oxidized in solution. In certain embodiments, Applicants' composition includes Vitamin C in an encapsulated form. Such encapsulation includes ethylcellulose, high melting fats, waxes, and combinations thereof.

In other embodiments, Applicants' composition includes derivatives of Vitamin C, such as compound II.

II

In certain embodiments, Applicants' composition includes a mono sulfate ester or a mono phosphate ester of Vitamin C, i.e. compound II where R1 is selected from the group consisting of a sulfate group, a phosphate group, and mixtures thereof.

In certain embodiments, Applicants' composition includes derivatizing both the 2- and 3-hydroxy groups, such as compound III.

III

In certain embodiments, the R1 moiety of compound III is selected from the group consisting of hydrogen, a sulfate group, a phosphate group, and mixtures thereof. In certain embodiments, the R2 moiety of compound III is selected from the group consisting of hydrogen, a sulfate group, a phosphate group, and mixtures thereof. In certain embodiments, R1 and R2 are the same. In other embodiments, R1 and R2 differ.

In certain embodiments, Applicants' composition includes derivatizing the 2-, 3-, and 6-hydroxy groups, such as compound IV.

IV

In certain embodiments, the R1 moiety of compound IV is selected from the group consisting of hydrogen, a sulfate group, a phosphate group, and mixtures thereof. In certain embodiments, the R2 moiety of compound IV is selected from the group consisting of hydrogen, a sulfate group, a phosphate group, and mixtures thereof. In certain embodiments, the R3 moiety of compound IV is selected from the group consisting of hydrogen, a sulfate group, a phosphate group, and mixtures thereof. In certain embodiments Applicants' composition includes compound IV wherein R1, R2, and R3, are the same. In other embodiments, Applicants' composition includes compound IV wherein one or more of R1, R2, and R3, differ.

In certain embodiments, Applicants' composition includes derivatizing the 2-, 3-, and 5-hydroxy groups, such as compound V.

V

In certain embodiments, the R1 moiety of compound V is selected from the group consisting of hydrogen, a sulfate group, a phosphate group, and mixtures thereof. In certain embodiments, the R2 moiety of compound V is selected from the group consisting of hydrogen, a sulfate group, a phosphate group, and mixtures thereof. In certain embodiments, the R3 moiety of compound V is selected from the group consisting of hydrogen, a sulfate group, a phosphate group, and mixtures thereof. In certain embodiments Applicants' composition includes compound V wherein R1, R2, and R3, are the same. In other embodiments, Applicants' composition includes compound V wherein one or more of R1, R2, and R3, differ.

In certain embodiments, Applicants' composition includes derivatizing the 2-, 3-, 5-, and 6-hydroxy groups, such as compound VI.

VI

In certain embodiments, the R1 moiety of compound VI is selected from the group consisting of hydrogen, a sulfate group, a phosphate group, and mixtures thereof. In certain embodiments, the R2 moiety of compound VI is selected from the group consisting of hydrogen, a sulfate group, a phosphate group, and mixtures thereof. In certain embodiments, the R3 moiety of compound VI is selected from the group consisting of hydrogen, a sulfate group, a phosphate group, and mixtures thereof. In certain embodiments, the R4 moiety of compound VI is selected from the group consisting of hydrogen, a sulfate group, a phosphate group, and mixtures thereof. In certain embodiments Applicants' composition includes compound VI wherein R1, R2, R3, and R4, are the same. In other embodiments, Applicants' composition includes compound VI wherein one or more of R1, R2, R3, R4, differ.

Applicants have learned that oral administration of Vitamin C to cattle results in measurable Vitamin C in the blood in about 45 minutes. These blood levels reach a maximum level between about 45 minutes and about 2 hours. In certain embodiments, Applicants orally administer their composition to a meat-producing animal about 45 minutes prior to harvest. In certain embodiments, Applicants orally administer their composition to a meat-producing animal about 2 hours prior to harvest. In certain embodiments, Applicants orally administer their composition to a meat-producing animal about 6 hours prior to harvest. In certain embodiments, Applicants orally administer their composition to a meat-producing animal about 18 hours prior to harvest. In certain embodiments, Applicants orally administer their composition to a meat-producing animal about 24 hours prior to harvest. In certain embodiments, Applicants orally administer their composition to a meat-producing animal about 48 hours prior to harvest As those skilled in the art will appreciate, the timing of the oral administration of Applicants' composition is determined by a number of factors including, for example, the logistics of feeding, the number of head, the situs of administration, environmental factors such as ambient temperature and humidity, and the like. Applicants have found that oral administration of their composition from about 45 minutes to about 48 hours prior to harvest results in the advantages described below.

Examples I and II are presented to further illustrate to persons skilled in the art how to make and use the invention and to identify presently preferred embodiments thereof. These examples are not intended, however, as limitations upon the scope of the invention, which is defined only by the appended claims.

Example I

To study the dose/response efficacy of a one-time administration of Vitamin C to beef cattle on the water retention of various cuts of meat prepared post-harvest, Applicants' studied four (4) treatments. Those treatments were is administered orally to 4 head of cattle about 6 hours prior to harvest.

In a first control treatment, no Vitamin C was administered. In a second treatment, the animal's feed included about 50 grams of a phosphorylated Vitamin C sold in commerce by Roche Vitamins, Inc. under the name Rovimix® Stay-C®. In a third treatment, the animal's feed included about 100 grams of Rovimix® Stay-C®. In a fourth treatment, the animal's feed included about 150 grams of Rovimix® Stay-C®. Table I summarizes the results of this Example I.

In treatments 2, 3, and 4, the phosphorylated Vitamin C was disposed in about 200 grams of grapefruit pulp. That Vitamin C/grapefruit pulp was orally administered to each of the cattle as a one-time drench. In treatment 1, the control cattle were administered the normal diet.

TABLE 1

| | | Dosing of Vitamin C | | | |
|---|---|---|---|---|---|
| | Cut | 0 grams | 50 grams | 100 grams | 150 grams |
| Drip Loss | LD | 0.4238 | 0.1075 | 0.2787 | 0.5228 |
| | TRI | 0.505 | 0.2013 | 0.1538 | 0.2625 |
| Percent moisture | LD | 0.7133 | 0.7021 | 0.729 | 0.7307 |
| | SM | 0.7108 | 0.6522 | 0.7187 | 0.725 |
| | TRI | 0.7187 | 0.7019 | 0.7329 | 0.7339 |
| Total moisture | LD | 381.31 | 384.78 | 366.33 | 354.2 |
| | SM | 377.68 | 353.36 | 365.7 | 371.99 |
| | TRI | 375.49 | 376.45 | 361.8 | 399.11 |
| Free water | LD | 17.1684 | 10.6005 | 8.5375 | 21.3195 |
| | SM | 15.0464 | 19.4804 | 16.041 | 24.3147 |
| | TRI | 17.3646 | 22.731 | 8.6499 | 18.9904 |
| Bound water | LD | 82.8316 | 89.3995 | 91.4625 | 78.6805 |
| | SM | 84.9536 | 80.5196 | 83.959 | 75.6853 |
| | TRI | 82.6354 | 77.269 | 91.3501 | 81.0096 |
| Immobile water | LD | 65.6632 | 78.799 | 82.925 | 57.3609 |
| | SM | 69.9073 | 61.0392 | 67.918 | 51.3706 |
| | TRI | 65.2709 | 54.5381 | 82.7002 | 62.0192 |

By "LD," Applicants mean meat products comprising the Longissimus dorsi muscle. These cuts are sold in commerce as, for example, strip loins. By "SM," Applicants mean meat products comprising the Semimembranosus/adductor muscle. These cuts are sold in commerce as, for example, top round or inside round. By "TRI," Applicants mean products comprising the triceps brachii muscle sometimes called the shoulder clod. These cuts are sold in commerce as, for example, beef roasts.

It is known that retained water contributes to the juiciness and palatability of meat. The ability of meat to retain its water during application of external forces such cutting, heating, grinding and pressing is called the water holding capacity of meat.

Water is typically found in three (3) locations in meat. "Bound water" comprises water disposed near charged hydrophilic groups on muscle proteins. It is tightly bound and remains so even during application of severe mechanical or any other physical force.

"Immobilized water" comprises water that has less orderly molecular orientation with respect to one or more charged groups in muscle protein. The water molecules are disposed more distant from the protein molecules, and are attached to the bound water molecules, but the binding force is weaker as compared to bound water.

"Free water" is held in place by capillary forces. The orientation of free water molecules is independent of the charged groups.

"Drip Loss" refers to cellular weepage from meat products. Meat products are sold by weight. These meat products are often sold to retail outlets in a vacuum-sealed packages. Water released from such packaged meat products, i.e. "drip loss," is visible to the purchaser. Needless to say, such drip loss is undesirable.

Figure 1:
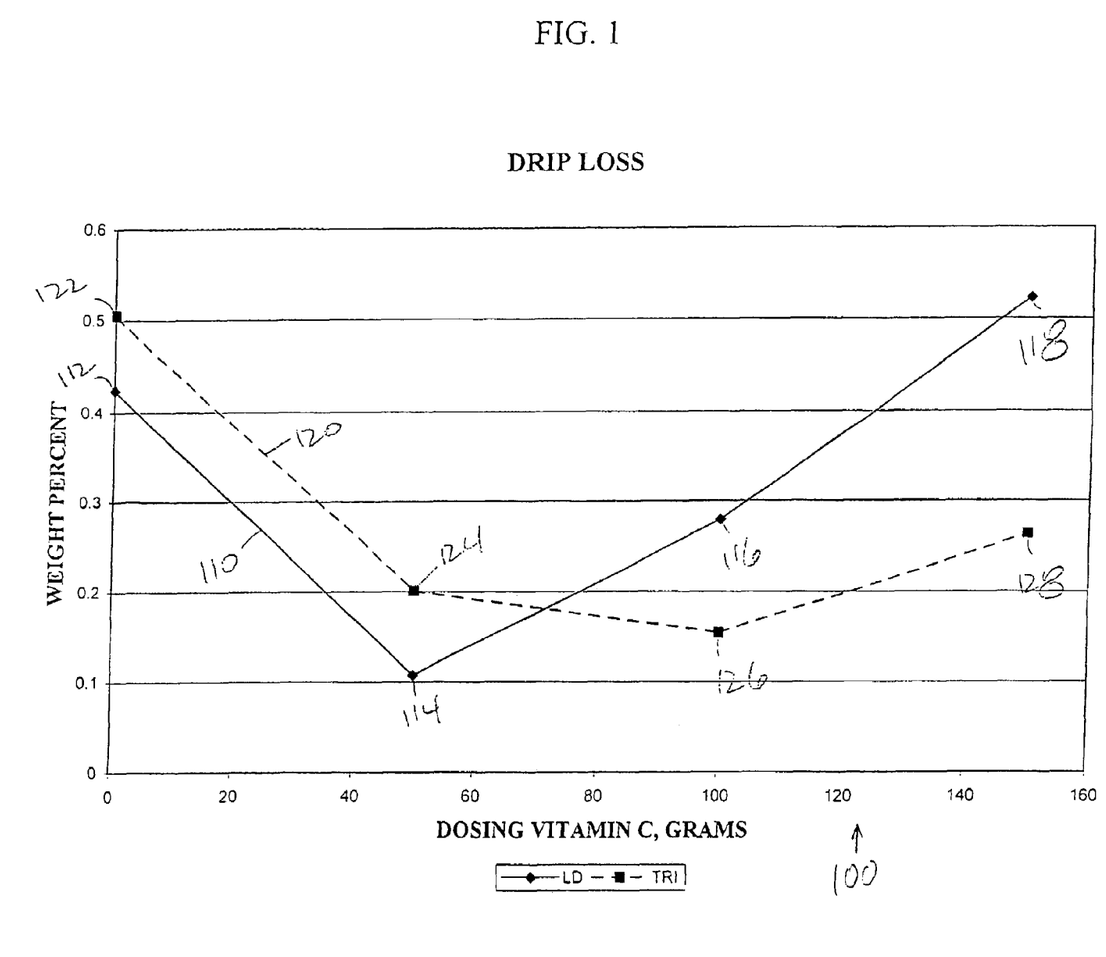
FIG. 1 is a graph showing decreased drip loss from meat products resulting from administering various dosings of Vitamin C to a meat-producing animal between about 6 to about 24 hours prior to harvest.

FIGS. 1, 2, 3, 4, and 5, graphically depict the data of Table I. Referring now to FIG. 1, graph 100 shows curves 110 and 120 which depict the drip loss measured for the four treatments described above for the LD and TRI meat portions, respectively. No administration of Vitamin C shows a drip loss of about 0.42% for LD cuts (point 112) and about 0.51% for TRI cuts (point 122). Curve 110 shows that administration of 50 grams of Vitamin C about 6 hours prior to harvest results in a decrease in the measured drip loss in LD cuts (point 114) and in TRI cuts (point 124). Administration of about 100 grams of Vitamin C results in a decrease drip loss over the controls in the LD cuts (point 116) and in the TRI cuts (point 126). Administration of 150 grams showed about the same drip loss as the control in LD cuts (point 118) and a decrease over the control in TRI cuts (point 128).

Figure 2:
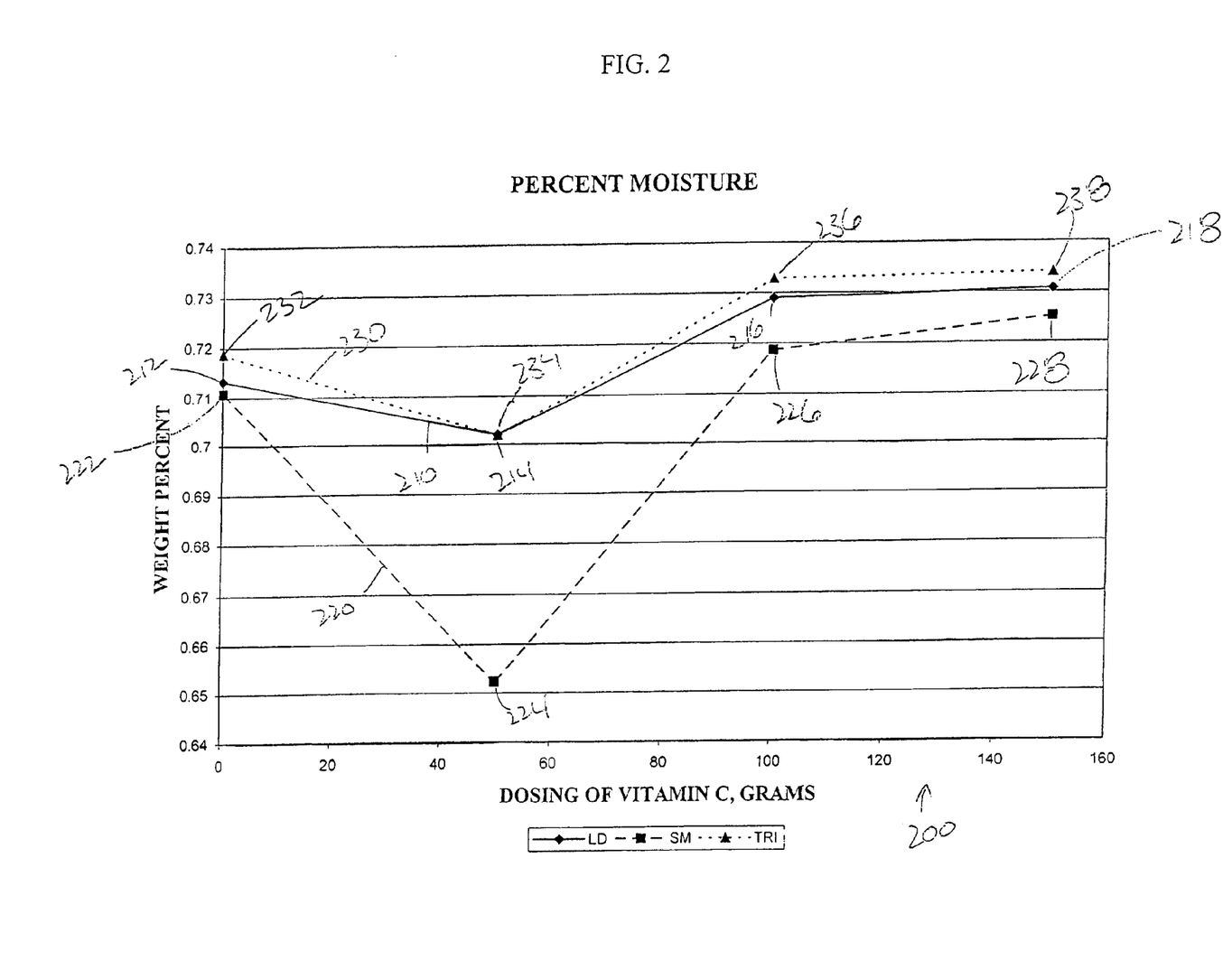
FIG. 2 is a graph showing increased water levels in meat products resulting from administering various dosings of Vitamin C to a meat-producing animal between about 6 to about 24 hours prior to harvest.

Referring now to FIG. 2, graph 200 shows the percent moisture in various meat cuts for 0, 50, 100, and 150, grams Vitamin C dosings about 6 hours prior to harvest. An increase in the percent water is desirable, as such an increase enhances the taste and tenderness of the meat. Curve 210 shows an increase over the control (point 212) in the percent moisture for both the 100 gram dosing (point 216) and the 150 gram dosings (point 218) in the LD cuts. Curve 220 shows an increase over the control (point 222) for both the 100 gram dosing (point 226) and the 150 gram dosing (point 228) in SM cuts. Curve 230 shows an increase over the control (point 232) for both the 100 gram dosing (point 236) and the 150 gram dosing (point 238) for the TRI cuts.

Figure 3:
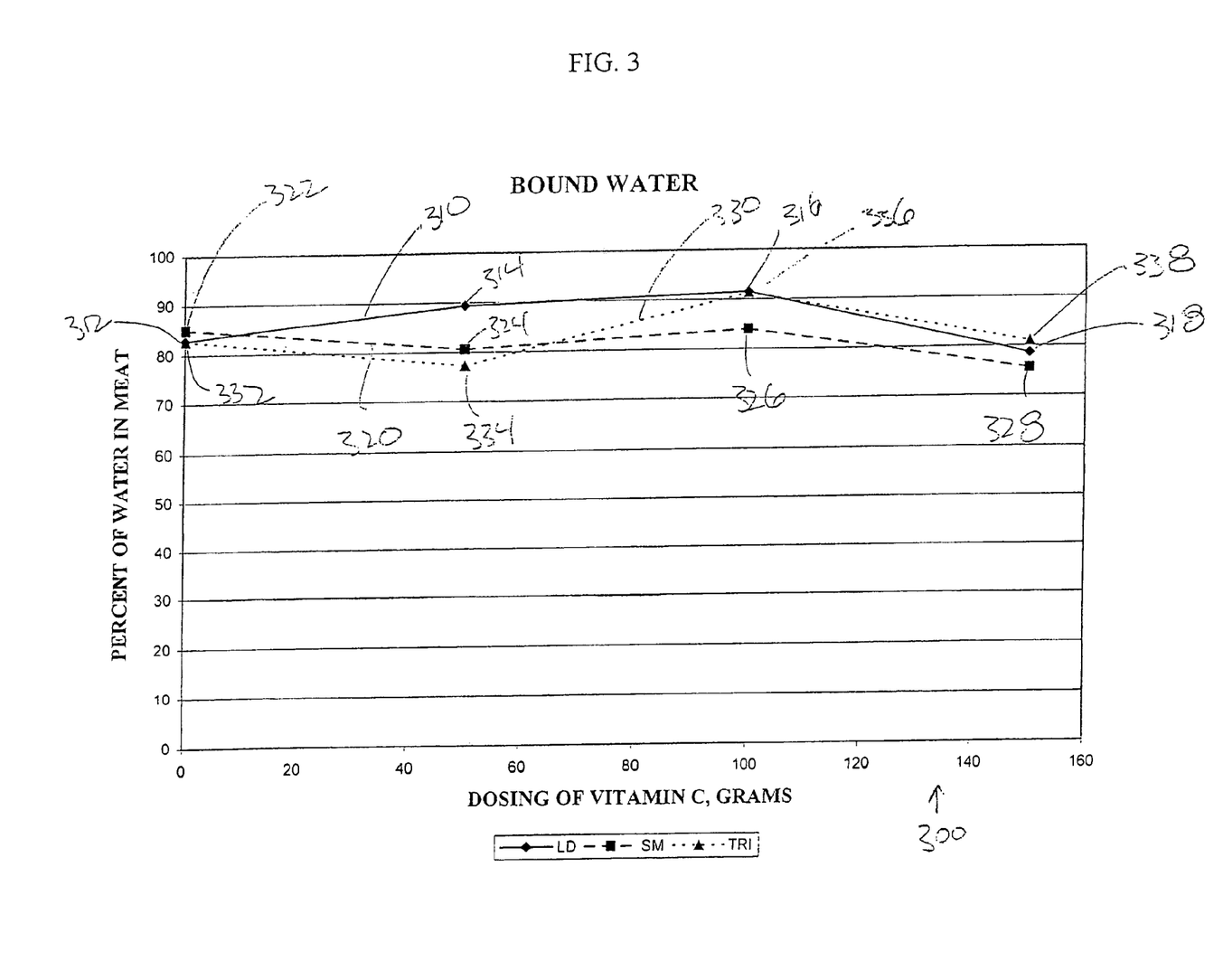
FIG. 3 is a graph showing increased bound water levels in meat products resulting from administering various dosings of Vitamin C to a meat-producing animal between about 6 to about 24 hours prior to harvest.

Referring now to FIG. 3, graph 300 shows the percent of water held as "bound water." An increase in the amount of bound water is desirable because such bound water is likely to remain in the meat product. Curve 310 shows an increase in bound water levels over the control (point 312) for the 50 gram dosing (point 314) and the 100 gram dosing (point 316) for the LD cuts. Curve 330 shows an increase in bound water levels over the control (point 332) for the 100 gram dosing (point 336) in TRI cuts.

Figure 4:
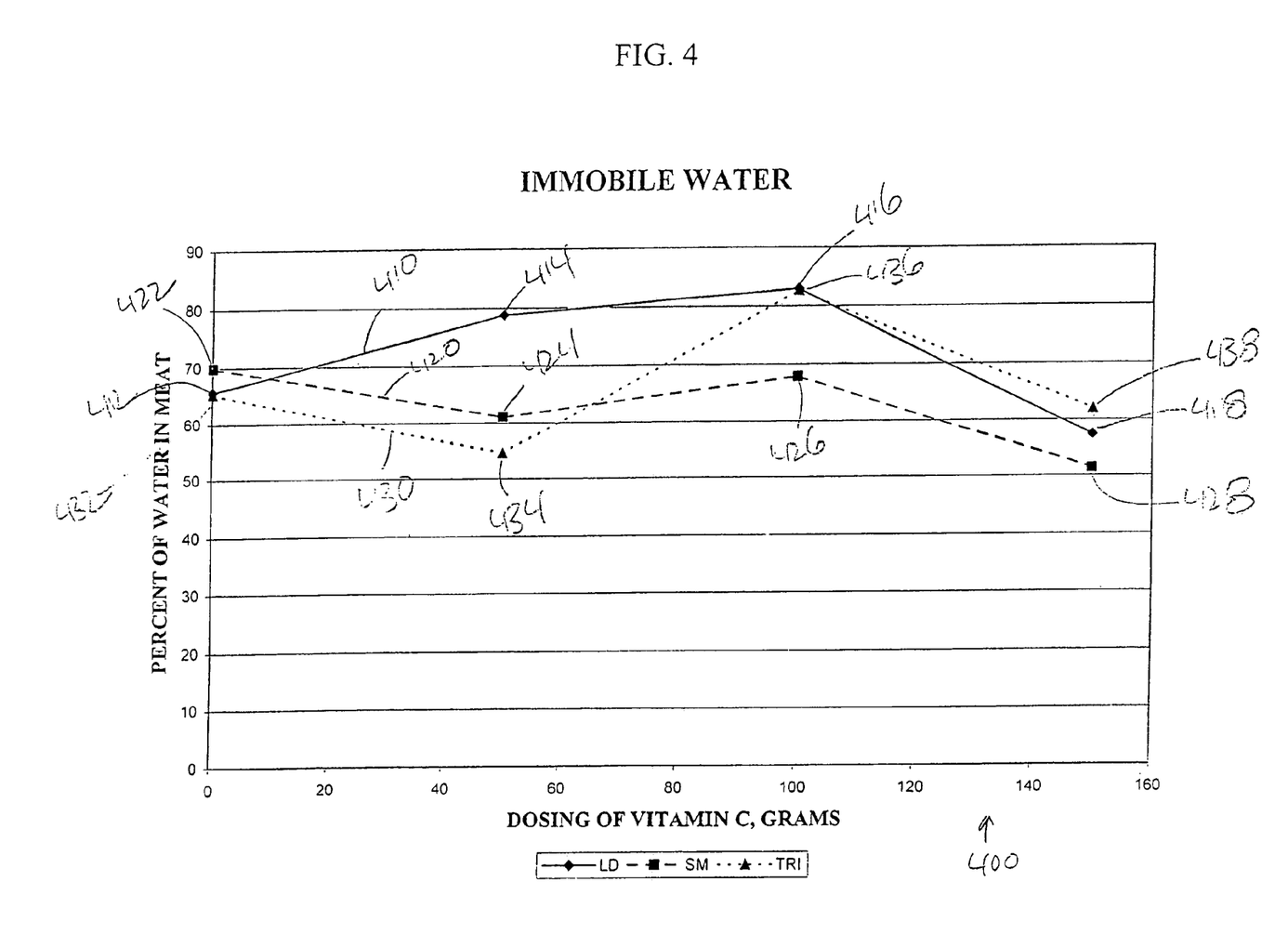
FIG. 4 is a graph showing increased immobile water levels in meat products resulting from administering various dosings of Vitamin C to a meat-producing animal between about 6 to about 24 hours prior to harvest.

Referring now to FIG. 4, graph 400 shows the percent of water held as "immobile water." An increase in the amount of such immobile water is desirable because that immobile water is likely to remain in the meat product. Curve 410 shows an increase in the immobile water over the control (point 412) for the 50 gram dosing and for the 100 gram dosing (point 416) in LD cuts. Curve 430 shows an increase in the immobile water over the control (point 432) for the 100 gram dosing (point 436).

Figure 5:
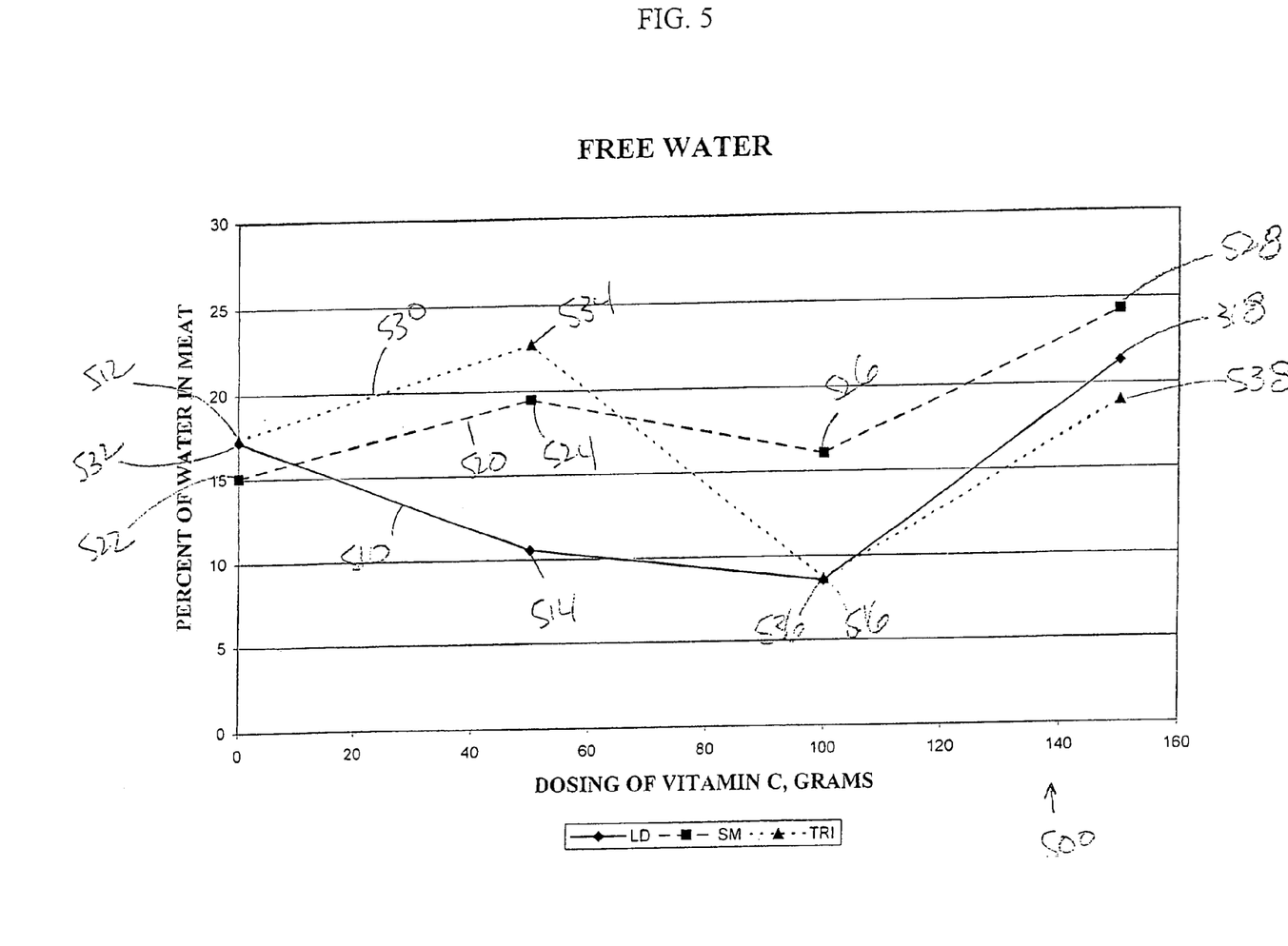
FIG. 5 is a graph showing decreased free water levels in meat products resulting from administering various dosings of Vitamin C to a meat-producing animal between about 6 to about 24 hours prior to harvest.

Referring now to FIG. 5, graph 500 shows the percent of water held as "free water." A decrease in free water levels in favor of increased bound water/immobile water is desirable.

Curve 510 shows a decrease in free water percent over the control (point 512) for the 50 gram dosing (point 514) and for the 100 gram dosing (point 516) for LD cuts. Curve 530 shows a decrease in the free water percent over the control (point 532) for the 100 gram dosing (point 536) for the TRI cuts.

Example II

The post-mortem production of lactic acid, and resulting drop in pH, lead to reduction of reactive groups on proteins as a result the binding sites are not available to water molecules. If the pH decreases to the isoelectric point, then there exist equal positive and negative charges on the myofilaments. This results in attraction of the charges to each other and reduction in number of reactive groups therefore only the left overs are available to attract water. As a result less water will be held.

While an increased pH for about 3 hours after harvest results in enhanced water retention, an increased pH after about 3 hours leads to the phenomenon called "dark cutters" described above. Therefore, what is needed is a method to increase the pH of meat products for about one (1) to three (3) hours after harvest, where the pH of the meat products thereafter decreases to less than about 6.

To study the dose/response efficacy of a one-time administration of Vitamin C to beef cattle on the pH of various cuts of meat prepared post-harvest, Applicants' studied four (4) treatments. Those treatments were is administered orally to 4 head of cattle about 6 hours prior to harvest. In a first control treatment, no Vitamin C was administered. In a second treatment, the animal's feed included about 50 grams of a phosphorylated Vitamin C sold in commerce by Roche Vitamins, Inc. under the name Rovimix® Stay-C®. In a third treatment, the animal's feed included about 100 grams of Rovimix® Stay-C®. In a fourth treatment, the animal's feed included about 150 grams of Rovimix® Stay-C®.

In treatments 2, 3, and 4, the phosphorylated Vitamin C was disposed in about 200 grams of grapefruit pulp. That Vitamin C/grapefruit pulp was orally administered to each of the cattle as a one-time bolus. In treatment 1, the control cattle were administered their normal diet.

Table II summarizes the results for top round cuts prepared post-harvest from cattle receiving a one-time dosing of phosphorylated Vitamin C about 6 hours pre-harvest.

TABLE II

Measured pH Of Top Round Cuts

| Time, Min. | Grams of Vitamin C Administered | | | |
| --- | --- | --- | --- | --- |
| | 0 | 50 | 100 | 150 |
| 0 | 6.57 | 6.70 | 6.70 | 6.64 |
| 30 | 6.27 | 6.46 | 6.44 | 6.47 |
| 60 | 5.98 | 6.12 | 6.36 | 6.20 |
| 90 | 5.74 | 5.84 | 6.05 | 5.91 |
| 120 | 5.60 | 5.75 | 5.81 | 5.78 |
| 150 | 5.54 | 5.60 | 5.59 | 5.67 |
| 180 | 5.52 | 5.53 | 5.55 | 5.57 |

Figure 6:
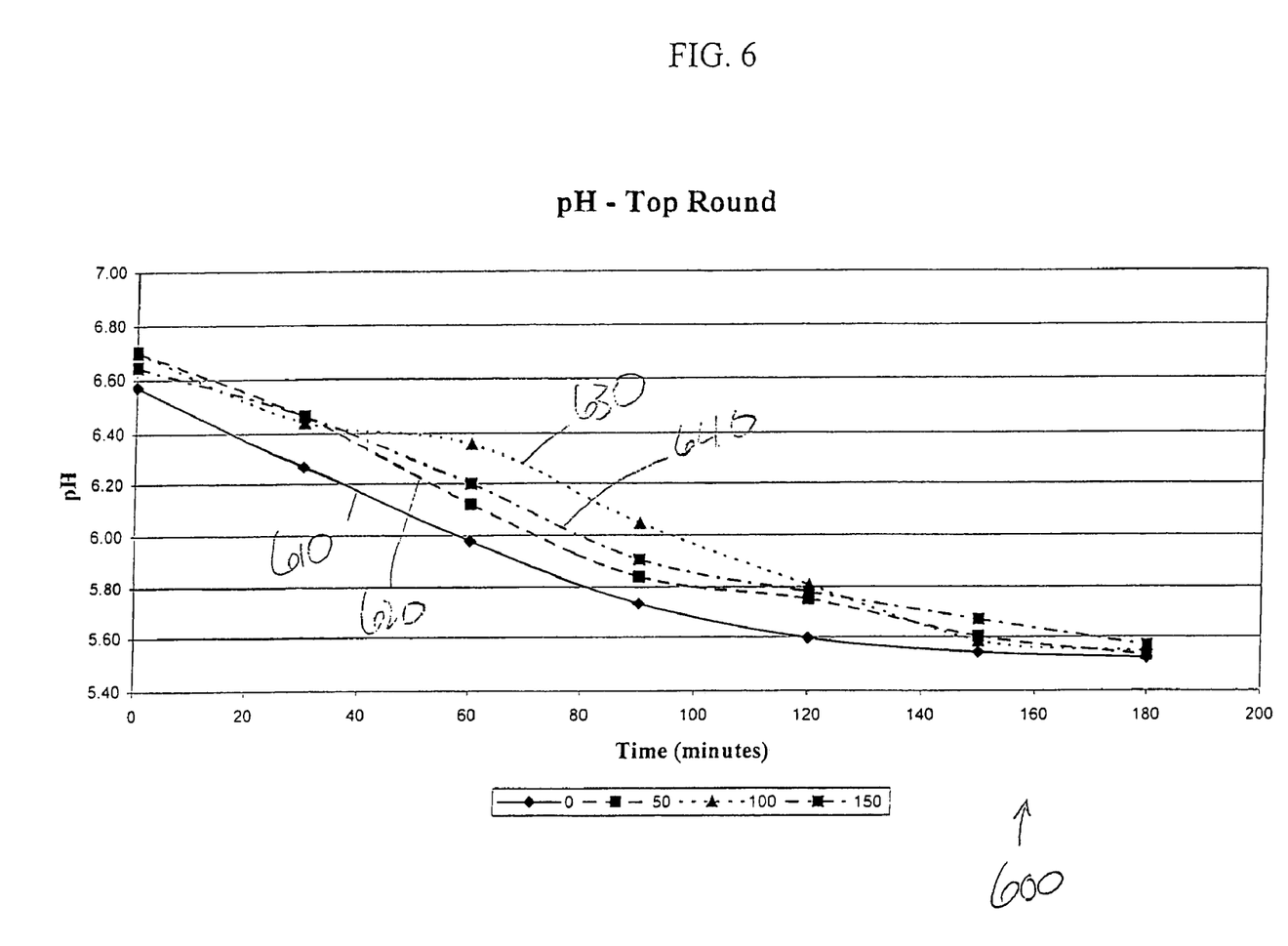
FIG. 6 is a graph showing increased pH levels for up to about 3 hours in top round cuts resulting from administering various dosings of Vitamin C to a meat-producing animal between about 6 to about 24 hours prior to harvest.

FIG. 6 graphically depicts the data of Table II. Referring now to FIG. 6, graph 600 shows the measured pH for top round meat cuts from 0 hours to 3 hours after harvest, where the meat cuts are prepared from cattle orally administered a one time dosing of 0, about 50, about 100, or about 150, grams of phosphorylated Vitamin C about 6 hours prior to harvest. Curve 610 comprises the control data, i.e. the pH for top round cuts obtained from cattle dosed with 0 grams of phosphorylated Vitamin C prior to harvest. Curve 620 comprises pH data for top round cuts obtained from cattle dosed with about 50 grams of phosphorylated Vitamin C prior to harvest.

Curve 630 comprises pH data for top round cuts obtained from cattle dosed with about 100 grams of phosphorylated Vitamin C prior to harvest. Curve 640 comprises pH data for top round cuts obtained from cattle dosed with about 150 grams of phosphorylated Vitamin C prior to harvest.

A comparison of curves 620, 630, and/or 640, with control curve 610 shows that a one time dosing of cattle with about 50, about 100, or about 150, grams of phosphorylated Vitamin C about 6 hours prior to harvest results in an increased pH for about one to three hours post-harvest in the meat products obtained from those cattle. Thereafter, the pH of meat products obtain from these same cattle is substantially the same as the pH of meat products obtained from cattle that were not dosed with phosphorylated Vitamin C.

Table III summarizes the results for strip loin, i.e. T-bone, cuts prepared post-harvest from cattle receiving a one-time dosing of phosphorylated Vitamin C about 6 hours pre-harvest.

TABLE III

Measured pH Of Strip Loin

| Time, Min. | Grams of Vitamin C Administered | | | |
|---|---|---|---|---|
| | 0 | 50 | 100 | 150 |
| 0 | 6.63 | 6.78 | 6.78 | 6.76 |
| 30 | 6.32 | 6.45 | 6.45 | 6.36 |
| 60 | 6.20 | 6.22 | 6.25 | 6.22 |
| 90 | 5.85 | 6.00 | 6.02 | 6.07 |
| 120 | 5.71 | 5.83 | 5.78 | 5.88 |
| 150 | 5.44 | 5.75 | 5.76 | 5.66 |
| 180 | 5.49 | 5.67 | 5.59 | 5.50 |

Figure 7:
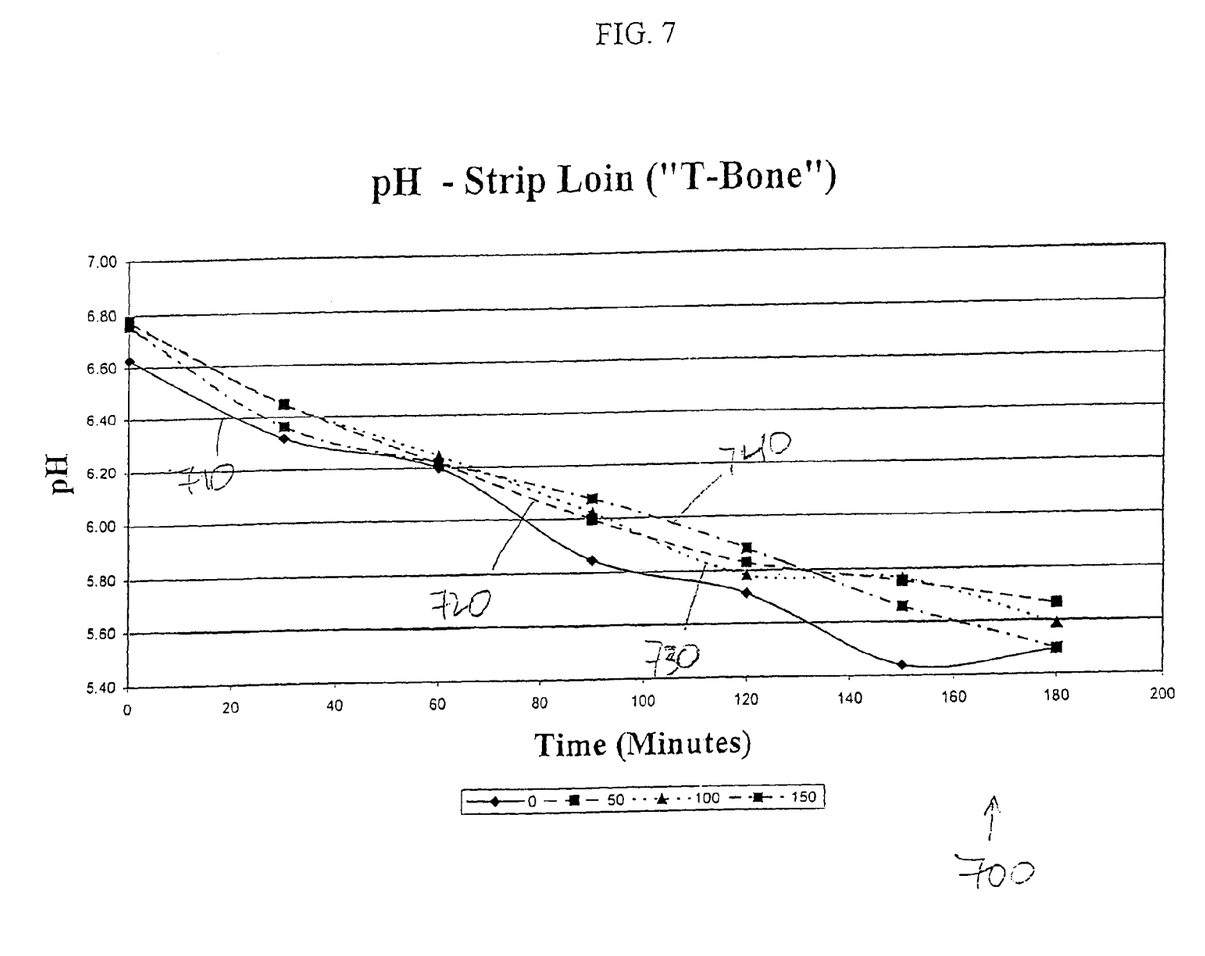
FIG. 7 is a graph showing increased pH levels for up to about 3 hours in strip loin cuts resulting from administering various dosings of Vitamin C to a meat-producing animal between about 6 to about 24 hours prior to harvest.

FIG. 7 graphically depicts the data of Table III. Referring now to FIG. 7, graph 700 shows the measured pH for strip loin cuts from 0 hours to 3 hours after harvest, where the meat cuts are prepared from cattle administered with a one time dosing of 0, about 50, about 100, or about 150, grams of phosphorylated Vitamin C about 6 hours prior to harvest. Curve 710 comprises the control data, i.e. the pH for strip loin cuts obtained from cattle dosed with 0 grams of phosphorylated Vitamin C prior to harvest. Curve 720 comprises pH data for strip loin cuts obtained from cattle dosed with about 50 grams of phosphorylated Vitamin C prior to harvest. Curve 730 comprises pH data for strip loin cuts obtained from cattle dosed with about 100 grams of phosphorylated Vitamin C prior to harvest. Curve 740 comprises pH data for strip loin cuts obtained from cattle dosed with about 150 grams of phosphorylated Vitamin C prior to harvest.

A comparison of curves 720, 730, and/or 740, with control curve 710 shows that a one time dosing of cattle with about 50, about 100, or about 150, grams of phosphorylated Vitamin C about 6 hours prior to harvest results for about one to three hours post-harvest in an increased pH in the meat products obtained from those cattle. Thereafter, the pH of meat products obtain from these same cattle is substantially the same as the pH of meat products obtained from cattle that were not dosed with phosphorylated Vitamin C.

Table IV summarizes the results for COD cuts, i.e. beef roasts, prepared post-harvest from cattle receiving a one-time dosing of phosphorylated Vitamin C about 6 hours pre-harvest.

TABLE IV

Measured pH Of Beef Roast

| Time, Min. | Grams of Vitamin C Administered | | | |
|---|---|---|---|---|
| | 0 | 50 | 100 | 150 |
| 0 | 6.54 | 6.82 | 6.73 | 6.77 |
| 30 | 6.28 | 6.41 | 6.43 | 6.44 |
| 60 | 6.22 | 6.19 | 6.19 | 6.26 |
| 90 | 6.02 | 6.11 | 6.05 | 6.06 |
| 120 | 5.88 | 6.10 | 5.96 | 5.91 |
| 150 | 5.83 | 6.01 | 5.89 | 5.80 |
| 180 | 5.87 | 5.87 | 5.83 | 5.79 |

Figure 8:
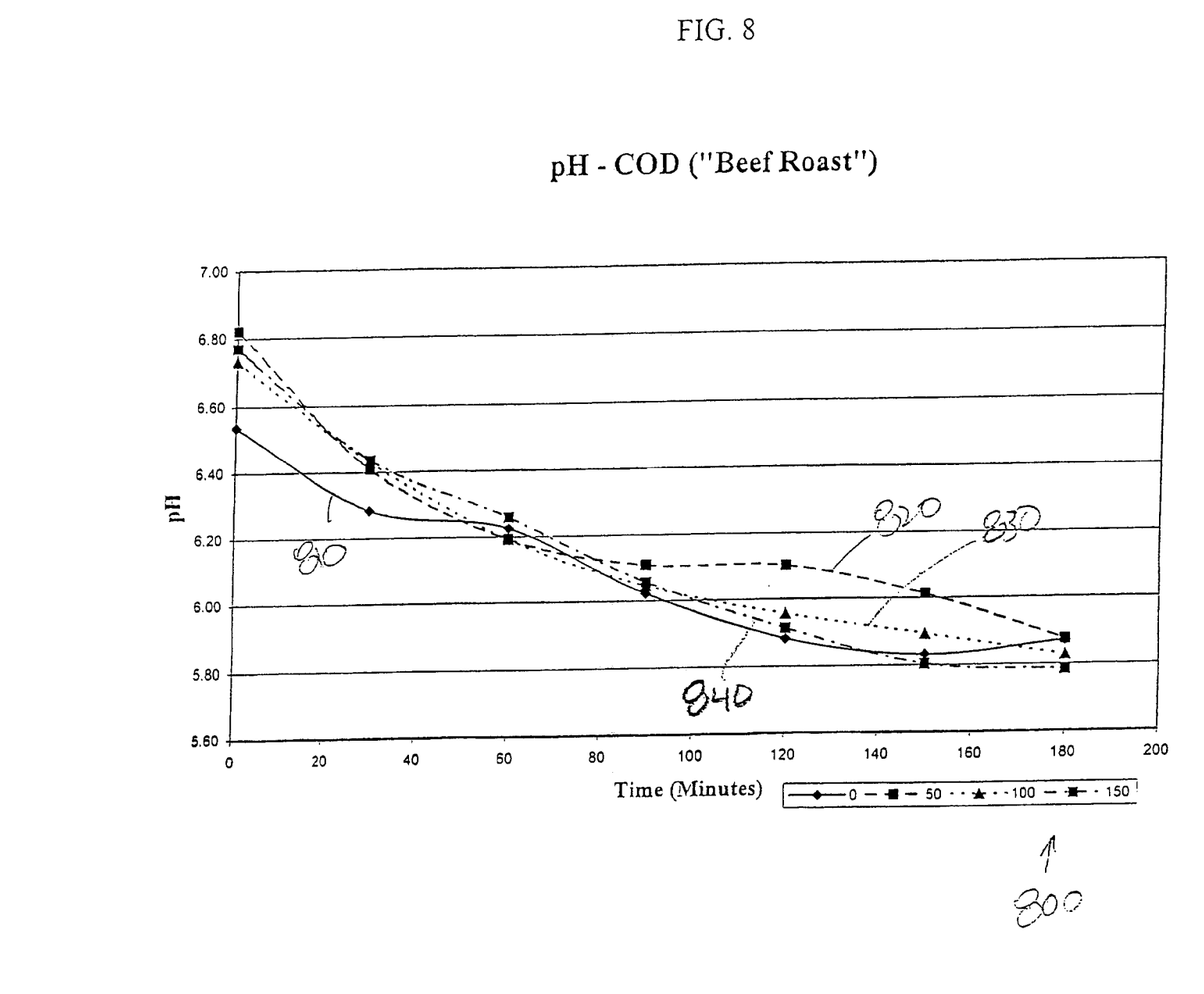
FIG. 8 is a graph showing increased pH levels for up to about 3 hours in beef roast cuts resulting from administering various dosings of Vitamin C to a meat-producing animal between about 6 to about 24 hours prior to harvest.

FIG. 8 graphically depicts the data of Table IV. Referring now to FIG. 8, graph 800 shows the measured pH for COD cuts from 0 hours to 3 hours after harvest, where the meat cuts are prepared from cattle administered with a one time dosing of 0, about 50, about 100, or about 150, grams of phosphorylated Vitamin C about 6 hours prior to harvest. Curve 810 comprises the control data, i.e. the pH for COD cuts obtained from cattle dosed with 0 grams of phosphorylated Vitamin C prior to harvest. Curve 820 comprises pH data for COD cuts obtained from cattle dosed with about 50 grams of phosphorylated Vitamin C prior to harvest. Curve 830 comprises pH data for COD cuts obtained from cattle dosed with about 100 grams of phosphorylated Vitamin C prior to harvest. Curve 840 comprises pH data for COD cuts obtained from cattle dosed with about 150 grams of phosphorylated Vitamin C prior to harvest.

A comparison of curves 820, 830, and/or 840, with control curve 810 shows that a one time dosing of cattle with about 50, about 100, or about 150, grams of phosphorylated Vitamin C about 6 hours prior to harvest results for about one to three hours post-harvest in an increased pH in the meat products obtained from those cattle. Thereafter, the pH of meat products obtain from these same cattle is substantially the same as the pH of meat products obtained from cattle that were not dosed with phosphorylated Vitamin C.

In certain embodiments, Applicants' composition includes certain materials derived from citrus fruits. Such citrus fruits include citron, orange, lemon, grapefruit, and lime. In certain embodiments, one or more of such citrus fruits are processed to yield citrus pulp and citrus molasses. Citrus pulp, corresponding to International Feed Number 4-01-237, comprises the peel and residue of the inside portions of the fruits which have been dried to produce a flaky product. In certain embodiments, Applicants' composition includes a citrus pulp having the properties recited in Table V.

TABLE V

FEED: CITRUS PULP, DEHYDRATE. W/O FINES, ORANGE, GRAPEFRUIT
BY PRODUCTS DRIED
INTERNATIONAL NUMBER: 4-01-237
TYPE: BY-PRODUCT ENERGY FEED
DRY MATTER: 91

| Animal Kind | (%) Ash | (%) CP | (%) Dig. | Dig. Units | DE (MCAL/lb) | ME (MCAL/lb) | NEm (MCAL/lb) | NEg (MCAL/lb) |
|---|---|---|---|---|---|---|---|---|
| CATTLE | 10.0 | 6.7 | 82.0 | TDN | 1.64 | 1.34 | 0.91 | 0.61 |

In Table V, above, and Table VI, below,
"CP" means crude protein,
"TDN" stands for the total digestible energy when consumed by cattle,
"DE" stands for digestible energy,
"ME" stands for metabolizable energy,
"NEm" stands for net energy - maintenance, and
"NEg" stands for net energy - growth.

Citrus molasses, corresponding to International Feed Number 5-01-241, comprises partially dehydrated juices obtained from the manufacture of citrus pulp. In general, such citrus molasses comprises about 45% or more total sugars. In certain embodiments, Applicants' composition includes cane molasses corresponding to International Feed Number 4-04-696. In certain embodiments, Applicants' composition includes cane molasses having the properties recited in Table V.

TABLE VI

FEED: SUGARCANE MOLASSES DEHYDRATED
INTERNATIONAL NUMBER: 4-04-696
TYPE: BY-PRODUCT ENERGY FEED
DRY MATTER: 94

| Animal Kind | (%) Ash | (%) CP | (%) Dig. | Dig. Units | DE (MCAL/lb) | ME (MCAL/lb) | NEm (MCAL/lb) | NEg (MCAL/lb) |
|---|---|---|---|---|---|---|---|---|
| CATTLE | 13.3 | 10.3 | 70.0 | TDN | 1.40 | 1.15 | 0.74 | 0.47 |

Example III

To study the dose/response efficacy of a one-time administration of Vitamin C to beef cattle about 16 hours prior to harvest on the yield of saleable meat products from those cattle, Applicants administered a single feeding of one pound of a composition comprising about 5 weight percent cane molasses corresponding to International Feed Number 4-04-696, about 21.5 weight percent Rovimix® Stay-C®, and about 73.5 weight percent dried citrus pulp corresponding to International Feed Number 4-01-237. In this composition, the dosing of phosphorylated Vitamin C is about 100 grams per head.

In a first treatment group, the above Rovimix® Stay-C® composition was fed to six groups of 100 heifers, i.e. total of 600 head, about 16 hours prior to harvest. In a second treatment group, Applicants administered a normal feeding to six groups of 100 heifers, i.e. total of 600 head, about 16 hours prior to harvest. In a third treatment group, the above Rovimix® Stay-C® composition was fed to six groups of 100 steers, i.e. total of 600 head, about 16 hours prior to harvest. In a fourth treatment group, Applicants administered a normal feeding to six groups of 100 steers, i.e. total of 600 head, about 16 hours prior to harvest.

Immediately after harvest, the hot carcass weight for each of the 2,400 cattle was determined. The hot carcass weight comprises the total saleable pounds obtained from each animal. A dressing percentage was calculated by dividing the measured hot carcass weight by the measured live weight, i.e. the weight of the animal prior to harvest. Table VII summarizes the data obtained in this Example III.

TABLE VII

| Group | Lot | Treatment | Avg. Hot Carcass Wt., Pounds | Avg. Dressing Percentage, % |
|---|---|---|---|---|
| I | 1 | 1 | 719 | 64.14 |
| I | 2 | 1 | 730 | 65.00 |
| I | 3 | 1 | 715 | 64.53 |
| I | 4 | 1 | 746 | 64.53 |
| I | 5 | 1 | 753 | 64.14 |
| I | 6 | 1 | 730 | 64.66 |
| II | 7 | 2 | 728 | 64.37 |
| II | 8 | 2 | 731 | 64.35 |
| II | 9 | 2 | 717 | 64.13 |
| II | 10 | 2 | 716 | 64.33 |
| II | 11 | 2 | 723 | 64.04 |
| II | 12 | 2 | 732 | 64.27 |
| III | 13 | 3 | 749 | 64.13 |
| III | 14 | 3 | 771 | 64.20 |
| III | 15 | 3 | 737 | 65.51 |
| III | 16 | 3 | 778 | 63.88 |
| III | 17 | 3 | 751 | 64.08 |
| III | 18 | 3 | 753 | 63.98 |
| IV | 19 | 4 | 740 | 63.57 |
| IV | 20 | 4 | 760 | 64.30 |
| IV | 21 | 4 | 779 | 64.75 |
| IV | 22 | 4 | 739 | 63.93 |
| IV | 23 | 4 | 758 | 63.97 |
| IV | 24 | 4 | 767 | 64.29 |

Using a Least Squares Analysis, Applicants determined an average hot carcass weight of 744.33 for the 1,200 cattle, i.e. all the heifers and steers, administered Applicants' phosphorylated Vitamin C/cane molasses/dried citrus pulp composition. Using this same analysis, Applicants determined an average hot carcass weight of 740.83 for the 1,200 cattle, i.e. all the heifers and steers, administered the regular diet.

Using a Least Squares Analysis, Applicants determined an average dressing percentage of 64.3983 for the 1,200 cattle, i.e. all the heifers and steers, administered Applicants' phosphorylated Vitamin C/cane molasses/dried citrus pulp composition. Using this same analysis, Applicants determined an average dressing percentage of 64.1917 for the 1,200 cattle, i.e. all the heifers and steers, administered the regular diet. There is a statistically significant difference between the average dressing percentage for the treatment groups administered Applicants' composition compared to the treatment groups administered the regular diet, with a p=0.0646.

The data of Table VII shows that a one time administration of one pound of Applicants' phosphorylated Vitamin C composition about 16 hours prior to harvest, results in an average hot carcass weight increase of 3.50 pounds per head. In addition, a one time administration of one pound of Applicants' phosphorylated Vitamin C composition about 16 hours prior to harvest, resulted in an average dressing percentage increase of 0.2066 percent per head.

While the preferred embodiments of the present invention have been illustrated in detail, it should be apparent that modifications and adaptations to those embodiments may occur to one skilled in the art without departing from the scope of the present invention as set forth in the following claims.

We claim:

1. A method to increase the hot carcass weight of cattle, comprising the steps of:
    providing a composition consisting of 73.5 weight percent dried citrus pulp, 21.5 weight percent Vitamin C, and 5 weight percent molasses;
    orally administering one pound of said composition one time to each of said cattle about 16 hours prior to harvest;
    harvesting said cattle; and
    preparing a hot carcass from each of said harvested cattle.

2. The method of claim 1, wherein said Vitamin C comprises a phosphorylated ascorbic acid.

3. The method of claim 2, wherein said phosphorylated ascorbic acid is selected from the group consisting of mono-phosphorylated ascorbic acid, di-phosphorylated ascorbic acid, tri-phosphorylated ascorbic acid, tetra-phosphorylated ascorbic acid, and mixtures thereof.

4. The method of claim 1, wherein said Vitamin C comprises a sulfate ester of ascorbic acid.

5. A method to increase the pH of a meat product obtained from cattle, comprising the steps of:
    providing a composition consisting of 73.5 weight percent dried citrus pulp, 21.5 weight percent Vitamin C, and 5 weight percent molasses;
    orally administering one pound of said composition one time to each of said cattle about 16 hours prior to harvest;
    harvesting said cattle; and
    preparing said meat product from each of said harvested cattle.

6. The method of claim 5, wherein said Vitamin C comprises a phosphorylated ascorbic acid.

7. The method of claim 6, wherein said phosphorylated ascorbic acid is selected from the group consisting of mono-phosphorylated ascorbic acid, di-phosphorylated ascorbic acid, tri-phosphorylated ascorbic acid, tetra-phosphorylated ascorbic acid, and mixtures thereof.

8. The method of claim 7, wherein said Vitamin C comprises a sulfate ester of ascorbic acid.

9. A method to increase the water content of a meat product obtained from cattle, comprising the steps of:
    providing a composition consisting of 73.5 weight percent dried citrus pulp, 21.5 weight percent Vitamin C, and 5 weight percent molasses;
    orally administering one pound of said composition one time to said animal about 16 hours prior to harvest;
    harvesting said animal; and
    preparing said meat product from each of said harvested cattle.

10. The method of claim 9, wherein said Vitamin C comprises a phosphorylated ascorbic acid.

11. The method of claim 10, wherein said phosphorylated ascorbic acid is selected from the group consisting of mono-phosphorylated ascorbic acid, di-phosphorylated ascorbic acid, tri-phosphorylated ascorbic acid, tetra-phosphorylated ascorbic acid, and mixtures thereof.

12. The method of claim 9, wherein said Vitamin C comprises a sulfate ester of ascorbic acid.

13. A method to decrease the drip loss from a meat product obtained from cattle, comprising the steps of:
    providing a composition consisting of 73.5 weight percent dried citrus pulp, 21.5 weight percent Vitamin C, and 5 weight percent molasses;
    orally administering one pound of said composition one time to each of said cattle about 16 hours prior to harvest;
    harvesting said cattle; and
    preparing said meat product from each of said harvested cattle.

14. The method of claim 13, wherein said Vitamin C comprises phosphorylated ascorbic acid.

15. The method of claim 14, wherein said phosphorylated ascorbic acid is selected from the group consisting of mono-phosphorylated ascorbic acid, di-phosphorylated ascorbic acid, tri-phosphorylated ascorbic acid, tetra-phosphorylated ascorbic acid, and mixtures thereof.

16. The method of claim 13, wherein said Vitamin C comprises a sulfate ester of ascorbic acid.

* * * * *